United States Patent
Markel

(10) Patent No.: US 12,130,287 B2
(45) Date of Patent: Oct. 29, 2024

(54) CEACAM1 BASED POINT-OF-CARE CANCER DIAGNOSTIC

(71) Applicant: Gal Markel, Haifa (IL)

(72) Inventor: Gal Markel, Haifa (IL)

( * ) Notice: Subject to any disclaimer, the term of this patent is extended or adjusted under 35 U.S.C. 154(b) by 123 days.

(21) Appl. No.: 16/883,298

(22) Filed: May 26, 2020

(65) Prior Publication Data

US 2020/0393459 A1 Dec. 17, 2020

Related U.S. Application Data

(63) Continuation of application No. 12/265,469, filed on Nov. 5, 2008, now Pat. No. 10,663,464.

(60) Provisional application No. 60/985,484, filed on Nov. 5, 2007.

(51) Int. Cl.
*G01N 33/543* (2006.01)
*G01N 33/574* (2006.01)

(52) U.S. Cl.
CPC . *G01N 33/54388* (2021.08); *G01N 33/57473* (2013.01); *G01N 2333/70596* (2013.01)

(58) Field of Classification Search
CPC .............. G01N 33/558; G01N 33/57473
See application file for complete search history.

(56) References Cited

U.S. PATENT DOCUMENTS

| | | | |
|---|---|---|---|
| 5,726,010 A | 3/1998 | Clark | |
| 6,183,972 B1 * | 2/2001 | Kuo | G01N 33/558 436/538 |
| 6,852,320 B2 | 2/2005 | Blumberg | |
| 2004/0047858 A1 | 3/2004 | Blumberg | |
| 2006/0008923 A1 | 1/2006 | Anderson | |
| 2006/0148097 A1 | 7/2006 | Yamaguchi | |
| 2007/0110668 A1 | 5/2007 | Markel | |

OTHER PUBLICATIONS

International Search Report and Written Opinion for International Patent Application No. PCT/IB08/05005, mailed Feb. 1, 2010.
International Search Report and Written Opinion for International Patent Application No. PCT/IB08/05005, mailed May 20, 2010.
Patent Cooperation Treaty, Notification Concerning Transmittal of International Preliminary Report on Patentability, in International Application No. PCT/IB2008/005005, dated May 20, 2020 (5 pages).
European Patent Office, Communication with extended European Search Report, in European patent application No. 08874385.1-2404 / 2208069 PCT/IB 2008005005, dated Jan. 4, 2012 (15 pages).
Alary, M., et al., "Evaluation of a Rapid Point-of-care test for the detection of gonococcal infection among female sex workers in Benin.", Sexually Transmitted Infections., Dec. 2006 LNKD-PUMDED:17215275, Dec. 5, 2006, vol. 82, suppl.5, pp. V29-V32, XP002665390, ISSN: 1368-4973. (4 pages).
Pham, Khoa V., et al., "Point-of-care detection of helicobacter pylori infection using a rapid urine antibody detection device", Gastroenterology, Elsevier, Philadelphia, PA, Apr. 1, 2005, vol. 128, No. 4, suppl. 2, XP009154672, ISSN: 0016-5085. (1 page).
Markel, Gal et al., "Systemic dysregulation of CEACAM1 in Melanoma Patients", Cancer Immunology, Immunotherapy, Springer, Berlin, DE., Jul. 25, 2009, vol. 59, No. 9, pp. 215-230, XP019757705, ISSN: 1432-0851. (16 pages).
Zhang, Gaiping et al., "Immunochramatographic lateral flow trip tests", Methods in Molecular Biology Human Press Inc., 999 Riverview Dr., Suite 208, Totowa, NJ, 07512-1165 USA Series: Methods in Molecular Biology (ISSN: 1064-3745(Print), 2009, p. 169-183, XP9154660 (16 pages).
Gray-Owen & Blumberg, Nat Rev. Immunol 2006; 6:433-46.
Kammerer, "The tumour suppressor gene CEACAM1 is completely but reversibly downregulated in renal cell carcinoma", J. Pathol., 204: 258-267, 2004.

* cited by examiner

*Primary Examiner* — Changhwa J Cheu
(74) *Attorney, Agent, or Firm* — McAndrews, Held & Malloy, Ltd.

(57) ABSTRACT

The present technology regards the utilization of CEACAM1 as a biomarker for cancer. In particular the present invention regards the detection and measurement of soluble CEACAM1 levels for the detection and diagnosis of melanoma.

1 Claim, 4 Drawing Sheets

FIGURE 4

|    | Low Risk patients | High Risk patients | Metastatic patients | Healthy donors |
|----|------|------|-------|------|
| 1  | 34.9 | 49.1 | 22.2  | 7.6  |
| 2  | 33.3 | 15.8 | 24.2  | 10.6 |
| 3  | 50.4 | 18.9 | 104.3 | 18.4 |
| 4  | 20.6 | 39.8 | 17.8  | 15.8 |
| 5  | 27.0 | 41.3 | 18.1  | 7.8  |
| 6  | 3.4  | 24.4 | 21.9  | 0.4  |
| 7  | 18.2 | 18.5 | 36.1  | 15.8 |
| 8  | 8.9  | 25.2 | 18.4  | 22.6 |
| 9  | 52.0 | 19.7 | 17.6  | 22.3 |
| 10 | 23.0 | 33.5 | 21.1  | 11.2 |
| 11 | 29.4 | 0    | 30.3  | 0.0  |
| 12 | 26.0 | 75.1 | 20.4  | 0.0  |
| 13 | 28.2 | 67.6 | 32.1  | 8.0  |
| 14 | 26.5 | 51.0 | 68.8  | 9.5  |
| 15 | 21.3 | 26.1 | 91.7  | 12.0 |
| 16 | 24.6 | 18.4 | 36.6  |      |
| 17 | 19.2 | 40.8 | 29.8  |      |
| 18 | 41.0 | 22.2 | 50.0  |      |
| 19 | 16.8 | 24.1 | 20.0  |      |
| 20 | 57.5 | 12.0 | 25.8  |      |
| 21 | 24.1 |      | 31.0  |      |
| 22 | 23.1 |      | 21.8  |      |
| 23 | 23.6 |      | 42.5  |      |
| 24 |      |      | 2.7   |      |

CEACAM1 BASED POINT-OF-CARE CANCER DIAGNOSTIC

CROSS-REFERENCE TO RELATED APPLICATIONS/INCORPORATION BY REFERENCE

The present application is related to and claims priority from U.S. Provisional Patent Application Ser. No. 60/985,484, filed Nov. 5, 2007, and titled "CEACAM1 Based Point-of-care cancer diagnostic," the contents of which are herein incorporated by reference in their entirety.

FIELD OF THE INVENTION

This invention relates generally to the field of cancer detection, and more specifically to the utilization of CEACAM1 as a biomarker for the point-of-care diagnosis of cancer.

BACKGROUND OF THE INVENTION

Cancer is a term for diseases in which abnormal cells divide without control. Cancer cells can invade nearby tissues and can spread to other parts of the body through the blood and lymph systems. There are several types of cancer, including without limitation, carcinoma which is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

The human carcinoembryonic Ag (CEA)3 protein family encompasses several proteins with different biochemical features. These proteins are encoded by 29 genes tandemly arranged on chromosome 19q13.2. CEA family genes have been classified into two major subfamilies, the CEA cell adhesion molecule (CEACAM) and the pregnancy-specific glycoprotein subgroups. The CEACAM proteins, which are part of the larger Ig superfamily, include CEACAM1, -3, -4, -5, -6, and -8. They share a common basic structure of sequentially ordered different Ig-like domain(s) and are able to interact with each other. For example, it has been reported that various CEACAM proteins, such as CEACAM1 or CEACAM5, exhibit both homophilic and heterophilic interactions.

CEACAM1 (CD66a), a transmembrane protein and member of the carcinoembryonicAgs family (belongs to IgSF), contains two ITIM sequences located within its cytosolic tail. CEACAM1 interacts with other known CD66 proteins (both homophilic and heterophilic interactions), including CD66a, CD66c, and CD66e proteins. It is expressed on a wide spectrum of cells, ranging from epithelial to hemopoietic origin. Among CD66 proteins tested, only the CD66a protein is expressed on the surface of activated CD16-negative NK cells.

Point-of-care testing refers to a medical test which is carried out at sites other than a central laboratory, and comprises testing at or near the site of patient care. The value added by Point-of-Care Diagnostics is significant, and includes for example: improved patient outcomes attributable to immediate on-site actionable healthcare resulting from immediate test results (i.e.—reduced time for start of treatment); access to areas lacking clinical laboratory infrastructures (i.e.—rural areas, disaster areas, and developing countries); and avoidance of sample identification and sample transport problems.

BRIEF SUMMARY OF THE INVENTION

The present technology generally regards methods for diagnosing cancer comprising the detection of soluble CEACAM1 in a biological sample. In one particular aspect, this technology relates to an immunochromatographic strip for the point-of-care detection of soluble CEACAM1 in a biological sample for the detection and prognosis of melanoma.

The present technology further regards a diagnostic device for point-of-care detection of cancer comprising a matrix material having an application zone wherein a test fluid is applied, the test fluid moving by capillary action into a reaction zone comprising a mobile phase having a first CEACAM1 binding element (i.e.—a first CEACAM1 antibody or fragment thereof) conjugated to a detectable moiety, the test fluid then moving by capillary action through the reaction zone into one or more capture zones having a stationary phase comprising a second CEACAM1 binding element (i.e. —a second CEACAM1 antibody or fragment thereof), the detection of CEACAM1 in the test sample being dependent upon the presence of said detectable moiety within the CEACAM1 capture zone.

BRIEF DESCRIPTION OF SEVERAL VIEWS OF THE DRAWINGS

FIG. 4. Presentation of data showing that soluble CEACAM1 is increased in melanoma patients.

DETAILED DESCRIPTION OF THE INVENTION

The present technology generally regards the use of soluble CEACAM1 for the diagnosis and for predicting the prognosis of cancer, including for example melanoma. The present technology also comprises in part a immunochromatographic strip for the point-of-care detection of CEACAM1 in a biological sample.

Figure 1:
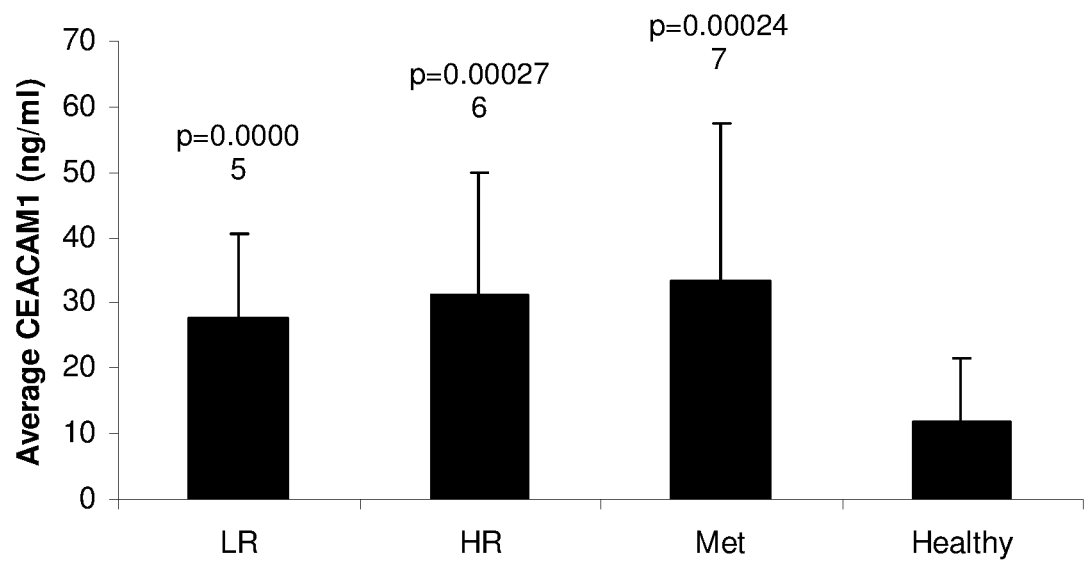
FIG. 1. Presentation of data showing that soluble CEACAM1 is increased in melanoma patients.

CEACAM1 appears as a soluble molecule in the peripheral blood. The present technology regards the diagnosis of cancer comprising the detection of soluble CEACAM1 in a biological sample. The data presented in FIG. 1 and FIG. 4 demonstrate that soluble CEACAM1 levels function as a biomarker for at least one type of cancer, namely melanoma (a form of skin cancer that begins in melanocytes (the cells that make the pigment melanin). As shown in FIG. 1, soluble CEACAM1 is increased in melanoma patients (LR (Low Risk); HR (High Risk); Met (Metastatic patients); healthy donors). Soluble CEACAM1 is quantified using a CEACAM1 specific sandwich ELISA. For example, the specific anti-CEACAM1 5F4 mAb can be used as capturing antibody. For detection, biotinylated Kat4c mAb can be used, followed by streptavidin-horseradish peroxidase (Jackson ImmunoResearch). Biotinylation of the Kat4c mAb can be performed with Sulfo-NHS-SS-Biotin (Pierce) according to the manufacturer's instructions. The quantification can then be calculated according to standard samples of CEACAM1-Ig fusion proteins.

Figure 2:
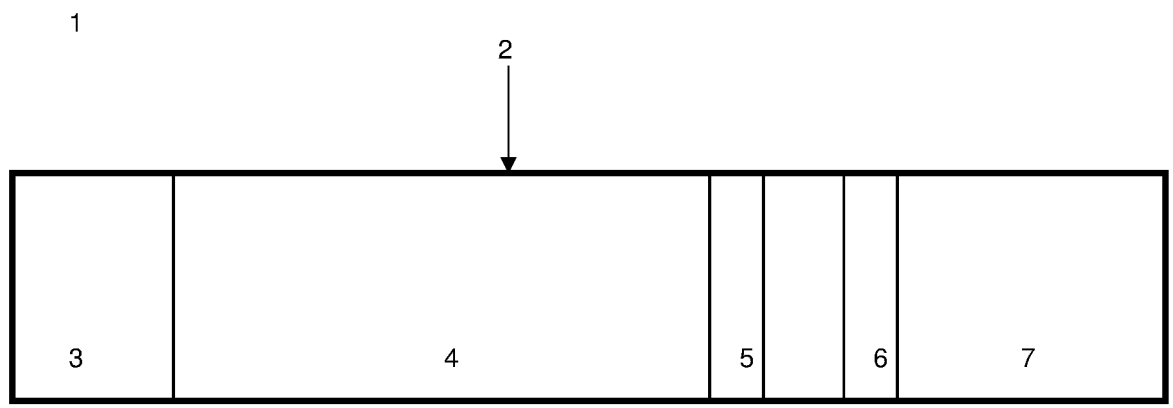
FIG. 2. Schematic representation of an immunochromatographic strip for the point-of-care detection of CEACAM1 in a biological sample.

FIG. 2 is an schematic illustration of one aspect of the present technology. Referenced generally as 1 is a immunochromatographic strip comprising a matrix material 2 having an application (or sample loading) zone 3, a reaction zone 4, a CEACAM1 capture zone 5, a control analyte capture zone 6, and an optional wicking pad 7.

The test fluid (and any CEACAM1 suspended or dissolved therein) is first brought into contacted with or applied to the application zone 3 of the immunochromatographic strip 1. The immunochromatographic strip 1 comprises a matrix material 2 which facilitates the test fluid moving by capillarity action from the application zone 3 through the reaction zone 4 and past the capture zones (CEACAM1 capture zone 5 and control analyte capture zone 6) to an optional wicking pad 7. Any detectable signal in the capture zones will reveal the presence of analyte (CEACAM1 or control).

The matrix material comprises a membrane material, for example nitrocellulose membrane, cellulose acetate membrane, glass-fiber membrane, or any combinations or derivatives thereof. The matrix material is porous, and any test liquid or sample applied to the matrix material at application zone 3 can move by capillary into the reaction zone 4 and continue to and/or past the capture zones 4 and 5.

The reaction zone 4 contains a mobile phase comprising a first CEACAM1 specific antibody (or fragment thereof) conjugated to a detectable moiety (e.g. —radioactive isotopes, enzymes, dyes, fluorescent dyes, dyed microspheres, affinity tag, or any combination or derivative thereof). The reaction zone 4 will also comprise, in mobile phase, a first control analyte specific antibody conjugated to a detectable moiety. When the test sample (and any CEACAM) moves by capillary action out of the application zone 3 and into the reaction zone 4, an antigen-antibody reaction ensues resulting in any CEACAM1 becoming bound (in mobile phase) by a first CEACAM1 specific antibody (or fragment thereof) conjugated to a detectable moiety. See FIG. 3.

The antigen (CEACAM1)-antibody reaction product formed within the reaction zone then migrates with the test liquid into one or more downstream capture zones having immobilized or stationary antibody. The CEACAM1 capture zone 5 comprises an immobilized or stationary phase second CEACAM1 binding element (e.g.—a second CEACAM1 antibody or fragment thereof) or CEACAM1 capture agent (e.g.—CEACAM1 capture antibody). The control analyte capture zone 6 also comprises an immobilized or stationary phase second control analyte binding element (e.g.—a second control analyte antibody or fragment thereof) or control analyte capture agent (e.g.—control analyte capture antibody). See FIG. 3.

Figure 3:
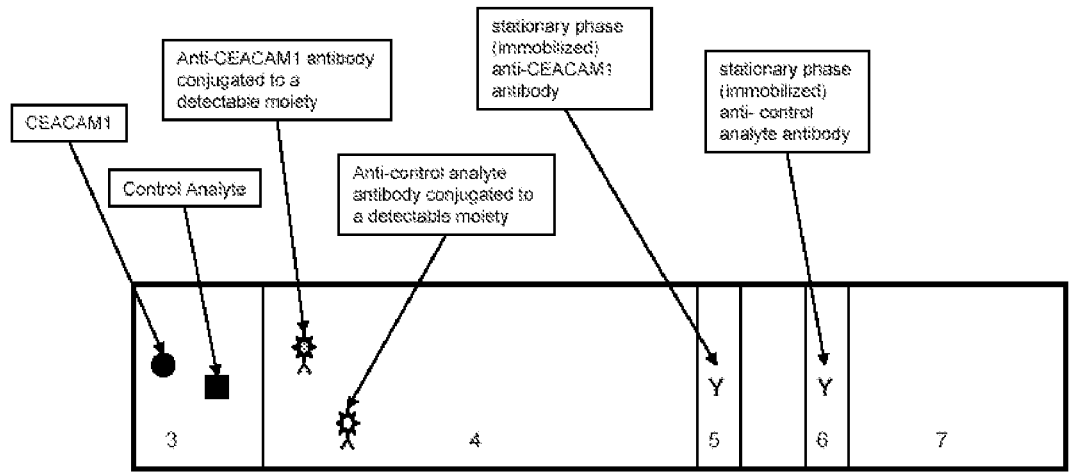
FIG. 3. Schematic representation of one embodiment of a lateral-flow point-of-care rapid detection system, for the detection and measurement of CEACAM1 in a test sample.
Figure 3:
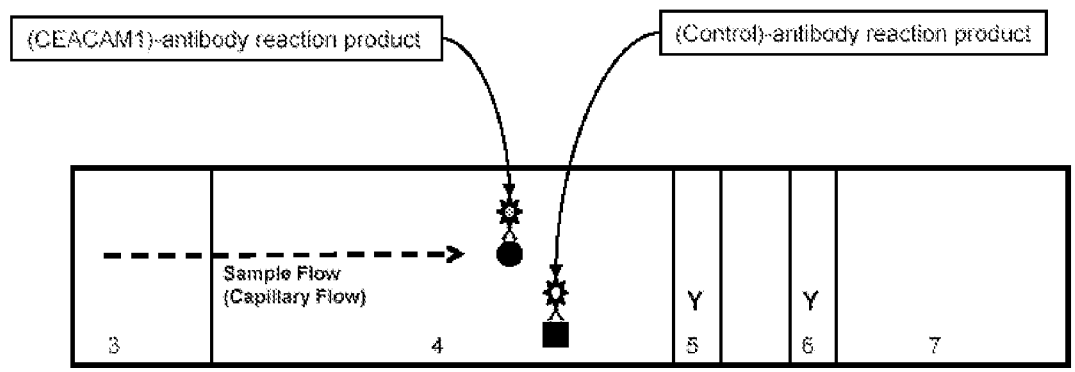
Figure 3:
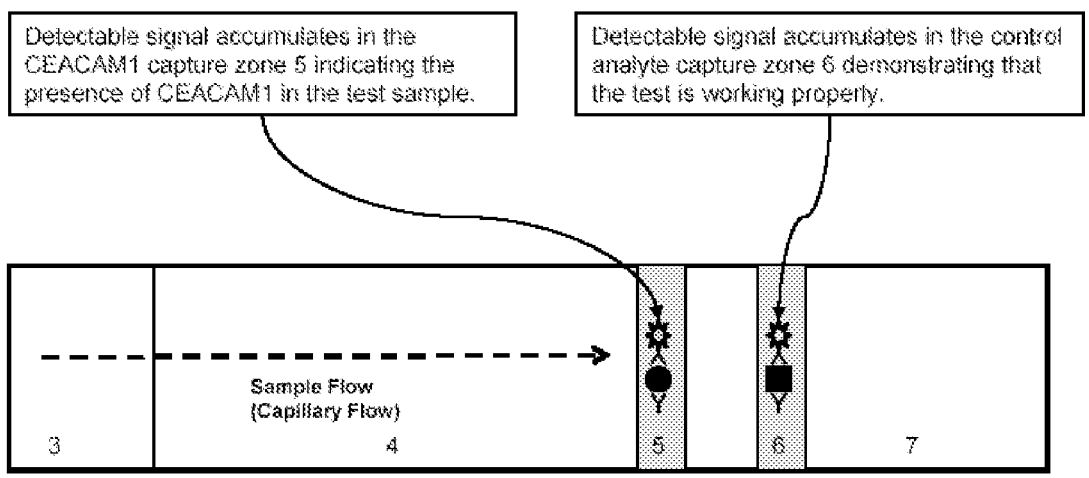

As a result of capillary flow from the application zone 3 through the reaction zone 4 and into the capture zones 5 and 6, a concentration of the detectable moiety builds within the capture zones, and the concentration of CEACAM1 in capture zone 5 (and control analyte(s) in capture zone 6) can then be assessed qualitatively or quantitatively with a suitable measuring instrument, or if dyes that are adsorbent in the visible range are used as the detectable moiety, can be perceived with the naked eye (FIG. 3).

The detection moiety can be radioactive isotopes, enzymes, dyes, fluorescent dyes, dyed microspheres, affinity tag, or any combination or derivative thereof.

The CEACAM1 binding agent (or capture agent) include without limitation an antibody (or fragment thereof) specific for CEACAM1. The antibody can be either polyclonal or monoclonal. Exemplar CEACAM1 specific antibodies include: Mouse monoclonal [29H2] to CEACAM1; Mouse monoclonal [GM8G5] to CEACAM1 (GM8G5 recognizes the Human CEACAM1 A2 domain); CEACAM1 antibody number 2037.00.02 (from Strategic Diagnostics Inc) binding CEACAM1 amino acids 35-134; the CEACAM1-specific antibody 4D1/C2; anti-CEACAM1 5F4 mAb; anti-CEACAM1 Kat4c mAb; or any combination or derivative thereof. The CEACAM1 binding agent can also be a member of the CEA protein family.

What is claimed is:

1. A device for the point-of-care detection of melanoma in a patient, the device configured to detect soluble Carcinoembryonic antigen-related cell adhesion molecule 1 (CEACAM1) level in a biological sample from the patient having melanoma, the device comprising:
    an immunochromatographic strip comprising a sample loading zone,
    a reaction zone having a mobile phase comprising a first CEACAM1 antibody conjugated to a detectable moiety; and
    a CEACAM 1 capture zone comprising an immobilized CEACAM1 binding agent;
        wherein said first CEACAM1 antibody binds to the CEACAM1 A2 domain, and said immobilized CEACAM1 binding agent is a member the CEA protein family; and
        wherein a detectable signal accumulates in the capture zone when the biological sample comprises at least 30 ng/ml soluble CECAM1.

* * * * *

UNITED STATES PATENT AND TRADEMARK OFFICE
CERTIFICATE OF CORRECTION

| | | |
|---|---|---|
| PATENT NO. | : 12,130,287 B2 | Page 1 of 1 |
| APPLICATION NO. | : 16/883298 | |
| DATED | : October 29, 2024 | |
| INVENTOR(S) | : Markel | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 213 days.

Signed and Sealed this
Second Day of September, 2025

Coke Morgan Stewart
*Acting Director of the United States Patent and Trademark Office*